United States Patent
Waller

(10) Patent No.: US 8,192,412 B2
(45) Date of Patent: Jun. 5, 2012

(54) PORTABLE FLUID STORAGE DEVICE

(76) Inventor: Larry Waller, Flossmoor, IL (US)

(*) Notice: Subject to any disclaimer, the term of this patent is extended or adjusted under 35 U.S.C. 154(b) by 781 days.

(21) Appl. No.: 12/284,692

(22) Filed: Sep. 24, 2008

(65) Prior Publication Data

US 2009/0187154 A1 Jul. 23, 2009

Related U.S. Application Data

(60) Provisional application No. 61/022,085, filed on Jan. 18, 2008.

(51) Int. Cl.
*A61M 1/00* (2006.01)
*A61F 5/44* (2006.01)

(52) U.S. Cl. ......... 604/347; 604/317; 604/327; 604/349

(58) Field of Classification Search .................. 604/327, 604/329, 347, 349
See application file for complete search history.

(56) References Cited

U.S. PATENT DOCUMENTS

| | | | | |
|---|---|---|---|---|
| 3,335,714 A | * | 8/1967 | Giesy | 600/574 |
| 3,635,091 A | * | 1/1972 | Linzer et al. | 600/580 |
| 3,727,244 A | * | 4/1973 | Collins | 4/144.3 |
| 4,020,843 A | | 5/1977 | Kanall | |
| 4,117,845 A | | 10/1978 | Brown | |
| 4,121,306 A | | 10/1978 | Bringman et al. | |
| 4,194,770 A | * | 3/1980 | Richards | 285/206 |
| 4,359,786 A | | 11/1982 | Rosberg et al. | |
| 5,511,557 A | * | 4/1996 | Hazard et al. | 600/573 |
| 5,551,097 A | | 9/1996 | Short | |
| 5,713,880 A | * | 2/1998 | Anderson | 604/349 |
| 6,026,519 A | | 2/2000 | Kaluza | |
| 6,230,515 B1 | * | 5/2001 | Wiesman | 62/457.1 |
| 6,684,414 B1 | * | 2/2004 | Rehrig | 4/144.1 |
| 6,805,690 B2 | * | 10/2004 | Ogden et al. | 604/352 |
| 7,335,189 B2 | * | 2/2008 | Harvie | 604/347 |
| 2002/0193760 A1 | * | 12/2002 | Thompson | 604/318 |
| 2003/0140409 A1 | | 7/2003 | Johnson | |
| 2004/0006321 A1 | * | 1/2004 | Cheng et al. | 604/349 |
| 2006/0100596 A1 | * | 5/2006 | Miskie | 604/349 |
| 2006/0111648 A1 | * | 5/2006 | Vermaak | 600/574 |
| 2008/0262448 A1 | * | 10/2008 | Mahalingam | 604/327 |

FOREIGN PATENT DOCUMENTS

| | | |
|---|---|---|
| GB | 871862 | 7/1961 |
| JP | 2007-275522 | 10/2007 |
| WO | 2004/087035 | 10/2004 |

OTHER PUBLICATIONS

Search Report in GB 0912738.2 dated Oct. 30, 2009 (1 page).
International Search Report and Written Opinion for PCT/US2009/04262, dated Sep. 15, 2009.

* cited by examiner

*Primary Examiner* — Leslie Deak
*Assistant Examiner* — Xin Xie
(74) *Attorney, Agent, or Firm* — Cardinal Law Group

(57) ABSTRACT

According to one aspect of the disclosure, a portable fluid storage device comprises a fluid impervious container having an interior space for the collection of human waste and a hollow tailpiece removably extending from the fluid impervious container and providing sealed fluid communication between an inlet end of the hollow tailpiece and the interior space. A cap is removably disposed at the inlet end of the hollow tailpiece and has a lumen disposed therethrough to provide a point of entry for the human waste into the portable fluid storage device. A flexible conduit is movably disposed within and removable from the hollow tailpiece and has an inlet end removably connected to an outlet end of the cap and an outlet end in fluid communication with the interior space of the fluid impervious container.

16 Claims, 5 Drawing Sheets

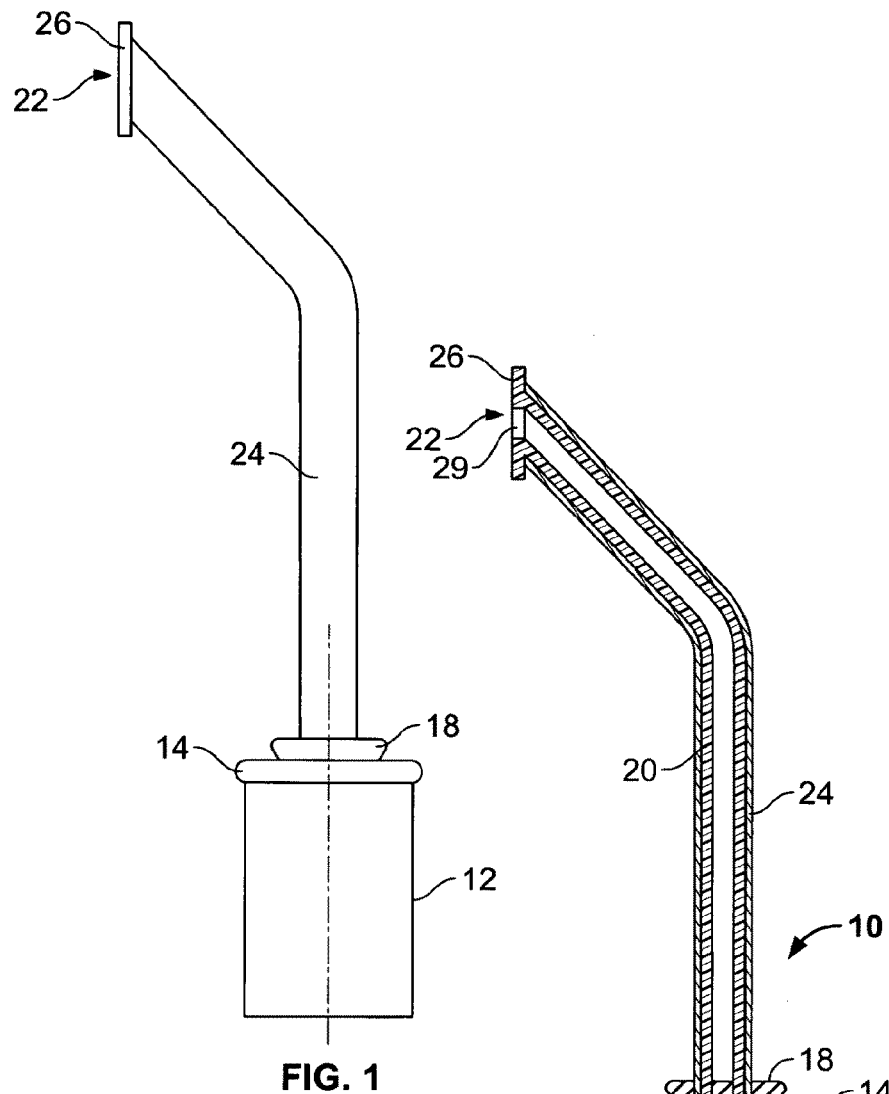
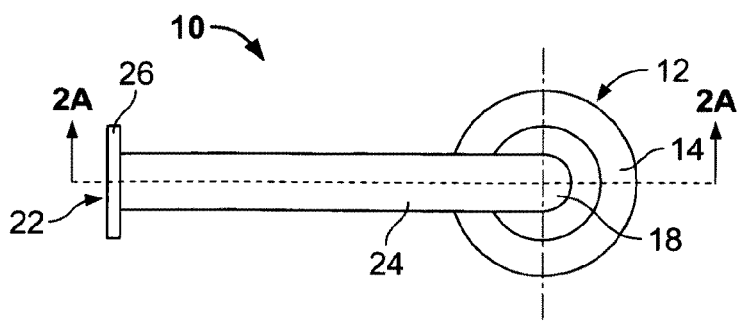
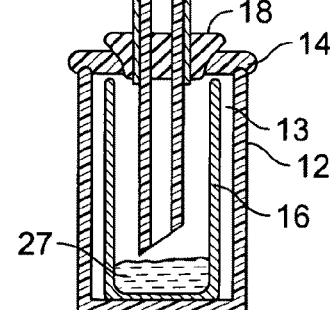

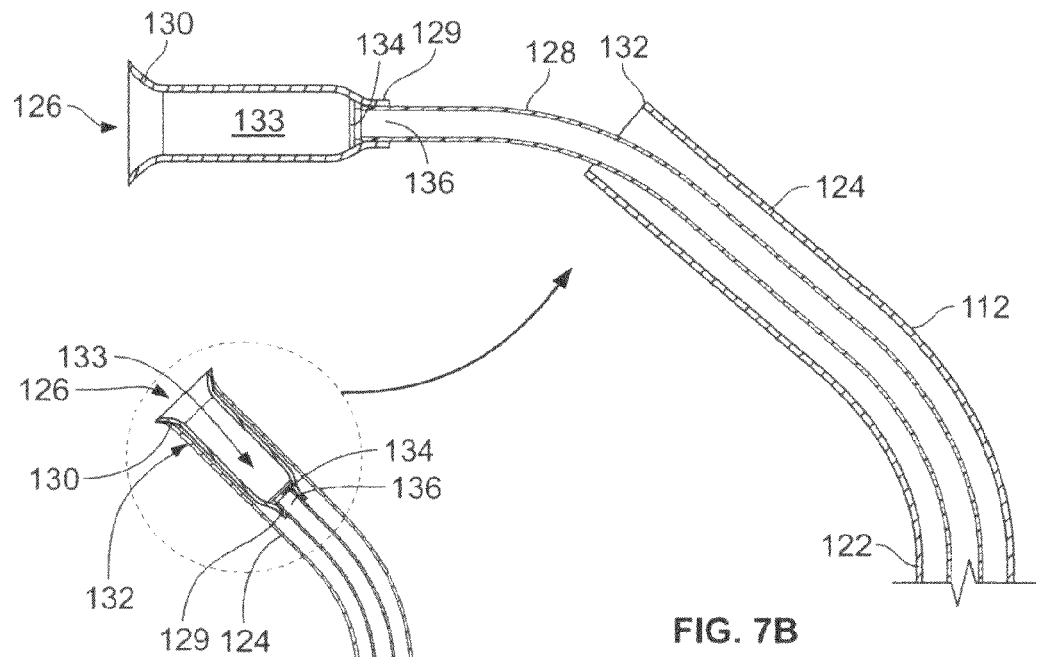
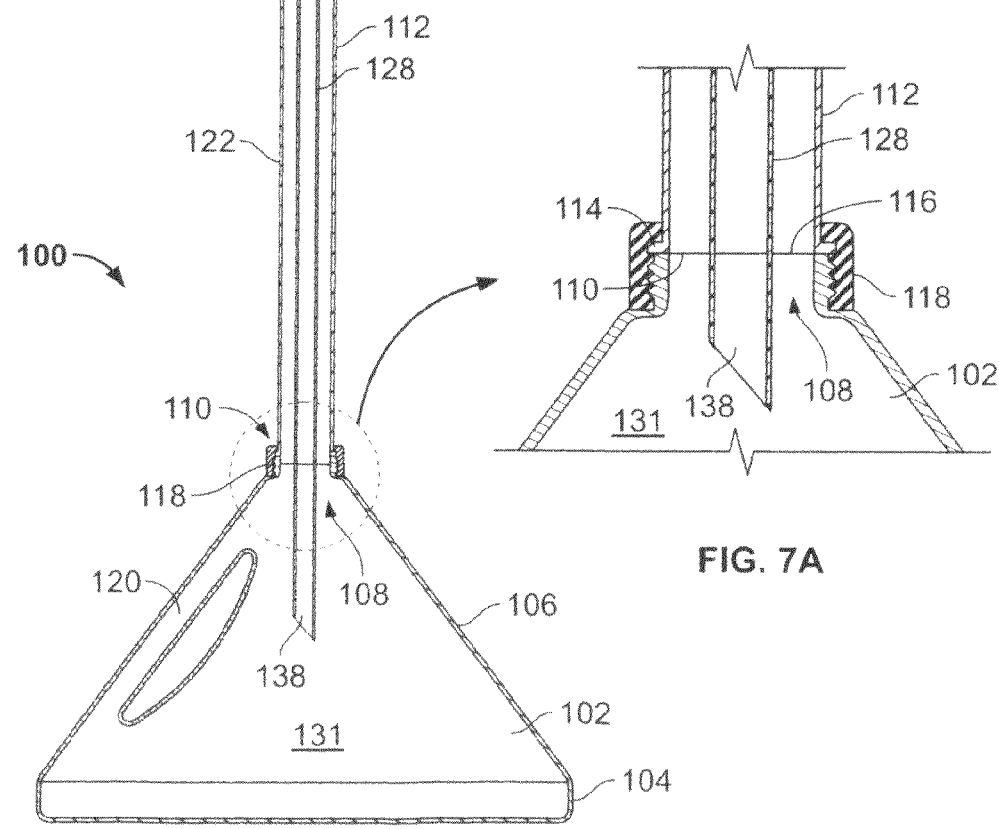

PORTABLE FLUID STORAGE DEVICE

CROSS REFERENCE TO RELATED APPLICATIONS

This disclosure claims the benefit of U.S. Provisional Application No. 61/022,085, filed Jan. 18, 2008, and which is incorporated by reference herein in its entirety.

BACKGROUND OF THE INVENTION

1. Field of the Invention

The present disclosure relates generally to apparatus and methods associated with portable storage devices for receiving and storing human or animal waste fluids.

2. Description of the Background of the Invention

Various portable fluid holding apparatus have been developed for use in collecting urine and other human waste fluids in the absence of suitable toilet facilities or to assist bedridden patients or individuals with other physical challenges. Customarily, when an individual is involved in circumstances of confinement or is subject to an interruption of sleep due to the need to urinate, a portable device for sanitarily collecting and storing human waste fluids for disposal has been shown to be useful.

Conventional portable urinals or bed pans may be generally funnel- or cylindrical-shaped at an opening which extends from a fluid second fluid impervious container used to store voided fluids. These portable urinals, while generally effective in receiving and storing human fluids, can be prone to leakage at connection points and, in hand-held models, may be susceptible to spilling issues. Other portable urinals may include large, cumbersome second fluid impervious containers connected to receiving apparatus by long hoses or tubes which can become tangled or easily cause spills if the receiving apparatus is not located physically above the second fluid impervious container, allowing gravity to reverse the desired flow of fluids. In still other, more complicated designs, motors can be used to pump fluids into a second fluid impervious container, but these features can unnecessarily complicate the design and introduce sanitary and safety concerns.

A similar problem of unsightliness exists in the range of typical portable fluid storage devices, which are primarily designed to be either hidden from view or used in a hospital/hospice setting. Conventional portable urinals are not adapted to contain inner fluid conduits and/or inner second fluid impervious containers, both designed to be removed from an outer structure and/or second fluid impervious container for disposal or cleaning of the inner parts which contact the waste fluid during its collection. Collected waste fluids are typically in plain sight within the second fluid impervious container, necessitating the desire for hiding such conventional portable urinals from view or otherwise allowing collected fluids to be visible.

It would be desirable to provide a portable fluid storage device that is designed to eliminate or minimize leakage and spilling issues and which contemplates inner portions which contact waste fluids and outer portions which may offer support and coverage for the inner portions.

SUMMARY OF THE DISCLOSURE

According to one aspect of the disclosure, a portable fluid storage device comprises a fluid impervious container having an interior space for the collection of human waste and a hollow tailpiece removably extending from the fluid impervious container and providing sealed fluid communication between an inlet end of the hollow tailpiece and the interior space. A cap is removably disposed at the inlet end of the hollow tailpiece and has a lumen disposed therethrough to provide a point of entry for the human waste into the portable fluid storage device. A flexible conduit is movably disposed within and removable from the hollow tailpiece and has an inlet end removably connected to an outlet end of the cap and an outlet end in fluid communication with the interior space of the fluid impervious container.

According to another aspect of the disclosure, a portable fluid storage device comprises a first fluid impervious container having a first interior space and a second fluid impervious container removably disposed within the first interior space and having a second interior space for the collection of human waste. A hollow tailpiece removably extends from the first fluid impervious container and provides sealed fluid communication between an inlet end of the hollow tailpiece and the first interior space. A cap is removably disposed at the inlet end of the hollow tailpiece and has a lumen disposed therethrough to provide a point of entry for the human waste into the portable fluid storage device.

According to yet another aspect of the present disclosure, a portable fluid storage device comprises a first fluid impervious container having a first interior space and a second fluid impervious container removably disposed within the first interior space and having a second interior space for the collection of human waste. A hollow tailpiece removably extends from the first fluid impervious container and provides sealed fluid communication between an inlet end of the hollow tailpiece and the first interior space. A cap is removably disposed at the inlet end of the hollow tailpiece and has a lumen disposed therethrough to provide a point of entry for the human waste into the portable fluid storage device. A flexible conduit is movably disposed within and removable from the hollow tailpiece and has an inlet end removably connected to an outlet end of the cap and an outlet end in fluid communication with the second interior space.

BRIEF DESCRIPTION OF THE DRAWINGS

FIG. 1 is a plan view of a portable fluid storage device according to one embodiment of the present disclosure;

FIG. 2 is a top view of the portable fluid storage device of FIG. 1;

FIG. 2A is a cross-sectional view of the portable liquid storage device of FIG. 2, taken generally along the lines 2A-2A in FIG. 2;

FIG. 7 is a cross-sectional view of the portable fluid storage device of FIG. 5, taken generally along the lines 7-7 of FIG. 6;

FIG. 7A is an enlarged view of a portion of the cross-sectional view of FIG. 7; and FIG. 7B is an enlarged view of another portion of the cross-sectional view of FIG. 7.

Figure 3:
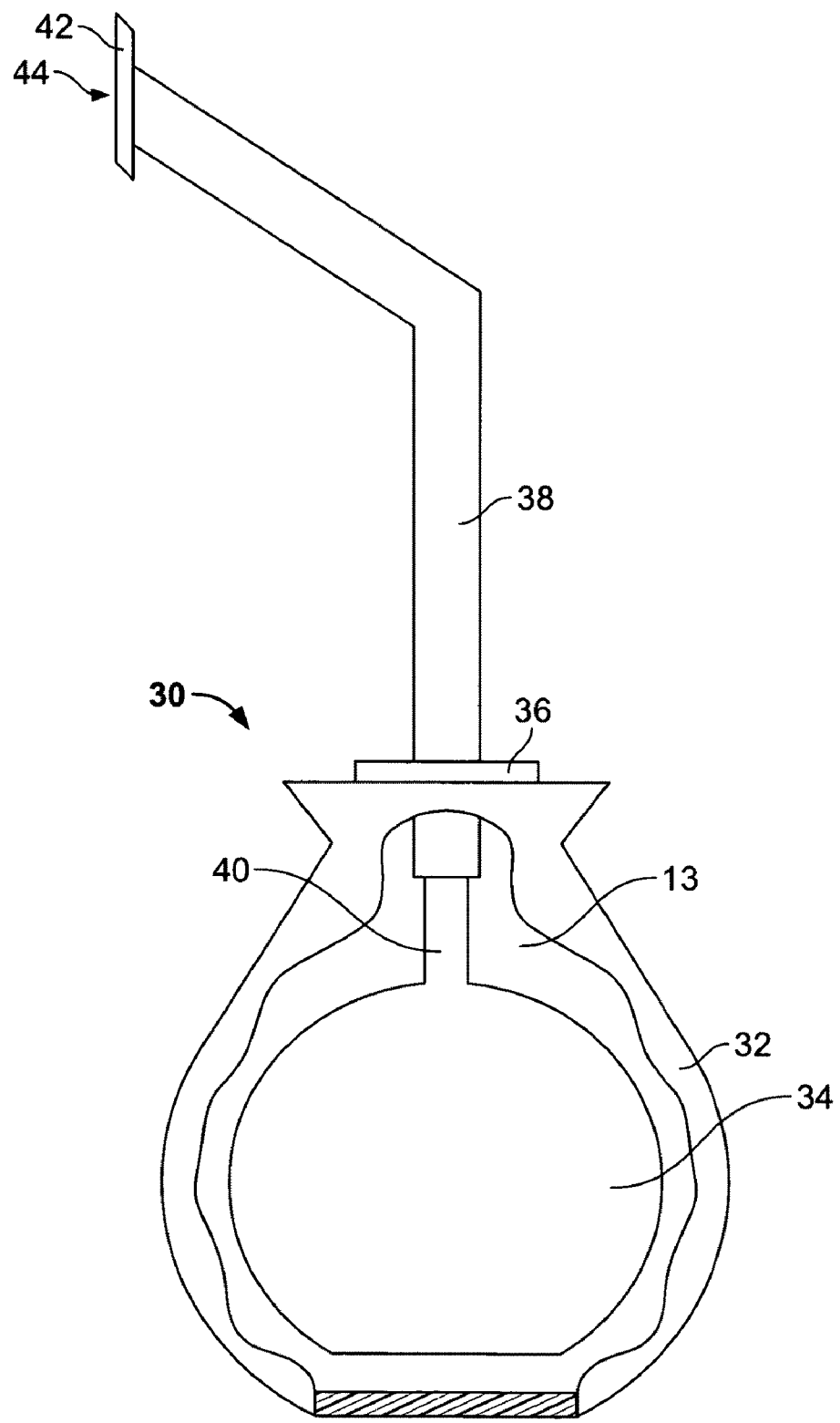
FIG. 3 is a partial cut-away plan view of another embodiment of a portable fluid storage device.

Other aspects and advantages of the present disclosure will become apparent upon consideration of the following

DETAILED DESCRIPTION

Referring now to FIGS. 1, 2, and 2A, an exemplary embodiment of a portable fluid storage device 10 is shown. The portable fluid storage device 10 includes a first fluid impervious container 12 with a lid 14. An open end of the first fluid impervious container 12 is sealingly covered by the lid 14, while a closed end of the first fluid impervious container 12 is designed with a substantially flat outer surface to be placed on a floor or other substantially flat surface. FIG. 2A illustrates the first fluid impervious container 12 and the lid 14 to each be made of plastic; however, the first fluid impervious container 12 is contemplated to be of any of a variety of shapes and to be constructed from any of a variety of materials, including but not limited to metal, plastic, fiberglass, clay, or porcelain, and combinations thereof, and the lid 14 may also be constructed of like materials or may be of a material different than the first fluid impervious container 12.

A second fluid impervious container 16 substantially fills an interior space 13 of the first fluid impervious container 12 and provides a protective covering for interior surfaces of the first fluid impervious container 12. The second fluid impervious container 16 in this embodiment is contemplated to be rigid, providing for an interference fit or for a gap, as illustrated in FIG. 2A, between the interior surfaces of the first fluid impervious container 12 and outer surfaces of the second fluid impervious container 16; alternately, the second fluid impervious container 16 may be pliable or bag-like and may be supported by the structure of the first fluid impervious container 12. Further, the second fluid impervious container 16 in particular embodiments may be fully removable from the first fluid impervious container 12 for disposal and cleaning of collected waste fluids. The second fluid impervious container 16 is contemplated to be of any variety of materials, including but not limited to, metal, plastic, rubber, fiberglass, clay, porcelain, and combinations thereof.

An opening, illustratively centrally located, is defined in the lid 14, in which a sealing gasket 18 may be placed, such as in an interference fit. The gasket 18 may also have an opening defined within for accepting a fluid conduit 20 within a hollow tailpiece 24 passing through the gasket 18 and into the second fluid impervious container 16. An outlet end of the fluid conduit 20 is positioned within the second fluid impervious container 16 to allow for the exit of fluids from the fluid conduit 20 into the second fluid impervious container 16. Extending upward from the horizontal plane of the closed end of the first fluid impervious container 12, and through the openings in the lid 14 and the gasket 18, the fluid conduit 20 is adapted to provide a point of entry 22 for human waste fluids at its inlet end. Such a point of entry 22 is contemplated to be at or about the height of a bed, chair, or other human support structure so that it is convenient for one to minimize movement to discharge waste fluids while providing ease of use in collecting the fluids.

In this embodiment, a hollow tailpiece 24 extends upward and in interference fit at an outlet end with the gasket 18 to cover the fluid conduit 20. In one embodiment, the hollow tailpiece 24 is of rigid construction and the fluid conduit 20 is flexible, allowing for the hollow tailpiece 24 to support the fluid conduit 20, as shown in FIG. 2A. The hollow tailpiece 24 is contemplated to be of plastic or any variety of metal, including but not limited to copper, brass, stainless steel, or other metals as known in the art. The fluid conduit 20 is contemplated to be of any variety of materials, including but not limited to plastic, rubber, or other material as may be desirable for fluid storage or as known in the art.

As can be appreciated by one skilled in the art, the fluid conduit 20 and the hollow tailpiece 24 may be of various rigidities—from extremely rigid to very flexible. The hollow tailpiece 24 may also include inlet and outlet ends and a straight section and a curved section located above the straight section, as shown in FIG. 1. In other embodiments, the specific configuration and angle of the hollow tailpiece 24 and the fluid conduit 20 may be altered without departing from the spirit and scope of the present disclosure. A stream of waste fluid discharged into the point of entry 22 is downwardly deflected against the interior walls of the fluid conduit 20 and directed to the second fluid impervious container 16. Illustratively, a cap 26 is positioned to fit within the fluid conduit 20 at the point of entry 22. The cap 26 includes a lumen 29 disposed therethrough and a flanged portion extending around the adjacent inlet end of the hollow tailpiece 24. Such a construction may allow for the cap 26 to provide a convenient, safe, and sanitary point of fluid entry while allowing for non-contamination of the hollow tailpiece 24 with waste fluids. It is contemplated that the cap 26 may be configurable to allow for use by either males or females, including in hospital and veterinary applications. In addition, differently constructed caps 26 providing a point of fluid entry 22 may be used interchangeably and fitted at the inlet end of the fluid conduit 20 when the portable fluid storage device is to be used by either a man or a woman.

In one embodiment, the first fluid impervious container 12 of the portable fluid storage device 10 is placed on a floor near or close to a bed or other support structure. The hollow tailpiece 24 and enclosed fluid conduit 20 extend upward to a height approximately equal to the height of the bed or other support structure. When the portable fluid storage device 10 is used, a subject is positioned near the point of entry 22 covered by the cap 26 and fluids are voided, which pass into the fluid conduit 20 without contaminating the hollow tailpiece 24. The fluids collected in the second fluid impervious container 16, may be dispersed in or allowed to mix with a fluid, gel, or solid 27. For example, water or a neutralizing, deodorizing, or antibacterial fluid, gel, or solid, as shown in FIG. 2A may be applied to an interior of the second fluid impervious container 16 prior to collection of waste fluid. Such a fluid, gel, or solid may also be used to weigh down the first fluid impervious container 12 to avoid tipping and spillage of fluids and for a dispersal of waste odors.

FIG. 3 shows an exemplary alternate embodiment of a portable fluid storage device 30 of the present disclosure. A first fluid impervious container 32 substantially similar to the first fluid impervious container 12 is disposed around a second fluid impervious container 34. As shown, a gasket 36 is fit into the first fluid impervious container 32 at a top opening, from wherein a hollow tailpiece 38 and a fluid conduit 40 extend. As is contemplated in the present disclosure, the fluid conduit 40 may be integral with the second fluid impervious container 34, as shown by FIG. 3, or it may be connected thereto by any of a variety of suitable means. The fluid conduit 40 may also extend into the second fluid impervious container 34, as in the portable fluid storage device 10, described hereinabove with regard to FIGS. 1, 2, and 2A. As illustrated in FIG. 3, the hollow tailpiece 38 may also extend through the gasket 36 and into the first fluid impervious container 32, as may also be the case for the portable fluid storage device 10.

The fluid conduit 40 and hollow tailpiece 38 are open at inlet ends opposite the first fluid impervious container 32; a point of entry 44 is provided by a lumen (not shown) disposed through a cap 42, which connects to the fluid conduit 40 at the point of entry and extends over the hollow tailpiece 38, protecting both the user from contact with the hollow tailpiece 38 and the hollow tailpiece 38 from contact with waste fluids. The cap 42 is substantially similar to the cap 26 described hereinabove with regard to FIGS. 1, 2, and 2A, and is contemplated to be formed of any number of materials such that it is not harmful to the touch by a user of the portable fluid storage devices 10 or 30 and may aid in guiding the user to direct a stream of fluid into the fluid conduits 20 or 40.

Figure 4:
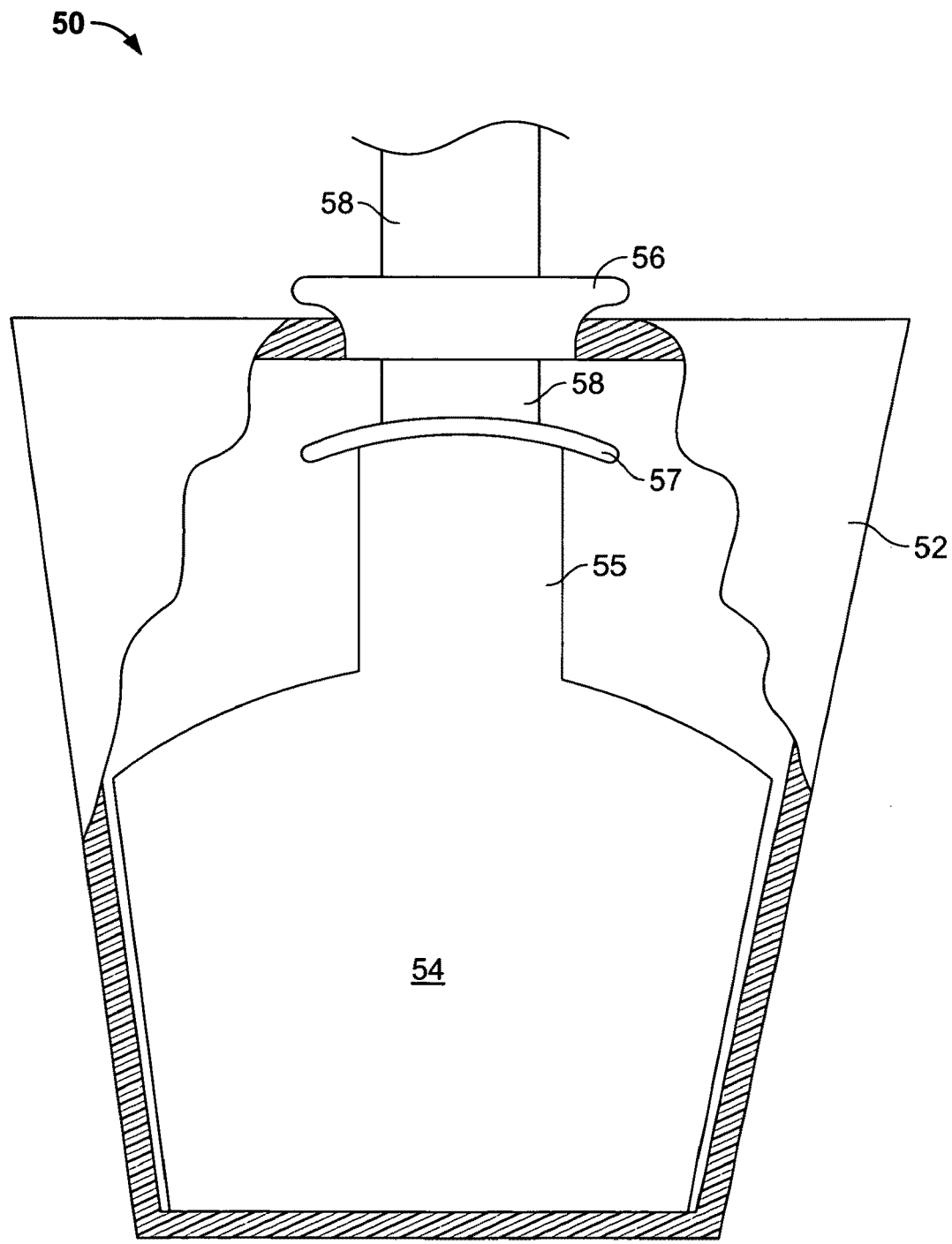
FIG. 4 is a partial cut-away plan view of an additional embodiment of a portable fluid storage device.
Figure 6:
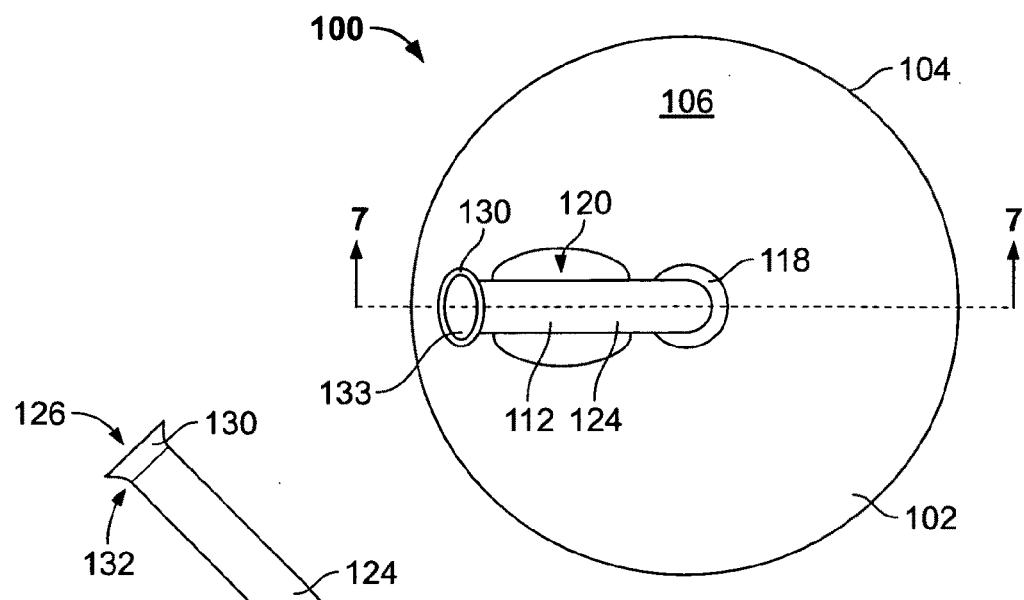
FIG. 6 is a top view of the portable fluid storage device of FIG. 5.

FIG. 4 shows a further embodiment of the portable fluid storage device 50 in which a first fluid impervious container 52 substantially similar to the first fluid impervious containers 12 and 32 is disposed around a second fluid impervious container 54. In this embodiment, the second fluid impervious container 54 is illustratively shown with an upper extent 55 having a flange 57 on an upper end thereof, such that the upper extent and the flange provide a handle for removing a full second fluid impervious container 54 from the first fluid impervious container 52 to be emptied and cleaned or disposed of. This embodiment also illustrates a gasket 56 substantially similar to the gaskets 18 and 36, and a hollow tailpiece 58 substantially similar to the hollow tailpieces 24 and 38. In this embodiment, a separate fluid conduit is not used, and waste fluid is collected through the hollow tailpiece 58 directly. As may be appreciated by one skilled in the art, a cap designed for the portable fluid storage device 50 may be fastened directly to the hollow tailpiece 58 and extend around an adjacent inlet end of the hollow tailpiece 58 at the point of entry for the waste fluids.

Illustratively, the second fluid impervious containers 16, 34, or 54 are designed to be removable from the first fluid impervious containers 12, 32, or 52, respectively, and cleaned or disposed of separately. In addition, the fluid conduits 20 or 40 may be designed to be removable from the first fluid impervious containers 12 or 32, respectively, the second fluid impervious containers 16 or 34, respectively, and the hollow tailpieces 24 or 38, respectively, and cleaned or disposed of separately. The hollow tailpiece 58 may also be designed to be removable from the first fluid impervious container 52 and the second fluid impervious container 54 and cleaned or disposed of separately.

Figure 5:
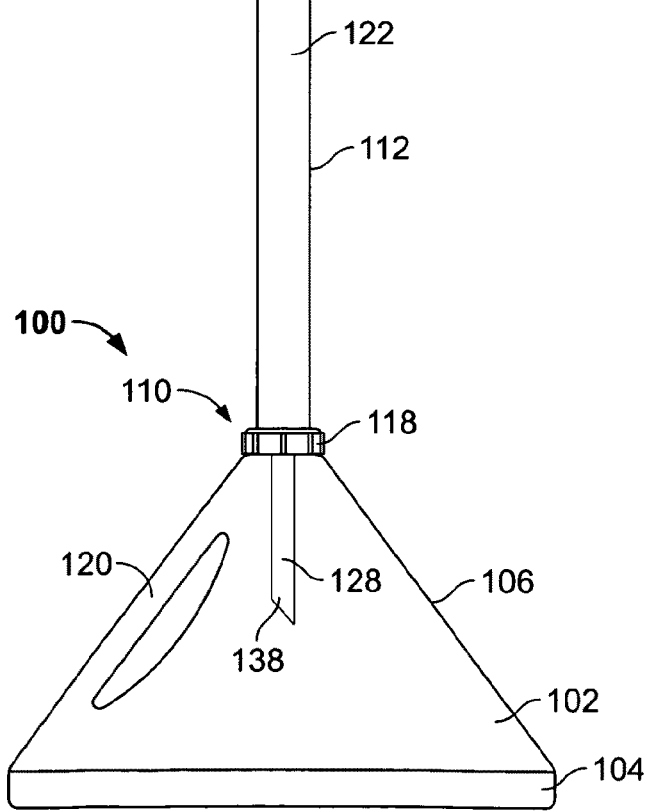
FIG. 5 is a plan view of a further embodiment of a portable fluid storage device.

Yet another embodiment of a portable fluid storage device 100 that includes a first fluid impervious container 102 is illustrated in FIGS. 5-7B. The first fluid impervious container 102 includes a broad bottom portion 104 and a continuous side wall 106 that tapers to an opening 108 at a top end 110 of the first fluid impervious container. The continuous side wall 106 is illustrated in FIG. 5 as transparent, but may be opaque or partially transparent and partially opaque to any degree desired. As best illustrated in FIGS. 7-7B, a hollow tailpiece 112 removably connects to the first fluid impervious container 102 at the top end 110 of the first fluid impervious container. For example, as shown in FIG. 7A, a flange 114 on an outlet end of the hollow tailpiece 112 is compressively sealed against a top surface 116 of the first fluid impervious container 102 by a compression nut 118. The hollow tailpiece 112 may be removably connected to the first fluid impervious container 102 by other methods (not shown), for example, a releasable snap fit, a frictional fit, a bayonet socket, or by other methods of removable connection as may be known in the art. The first fluid impervious container 102 further includes a handle 120 that facilitates emptying of the first fluid impervious container 102 of waste through the opening 108.

A first portion 122 of the hollow tailpiece 112 extends substantially vertically from the first fluid impervious container 102. A second portion 124 of the hollow tailpiece extends at least partially transverse to the first portion 122 such that a point of entry 126 includes a horizontal path for entry into the hollow tailpiece 112. A fluid conduit 128 is movably disposed within the hollow tailpiece 112. The fluid conduit 128 is removably connected to an outlet end 129 of a cap 130 that includes a lumen 133 disposed therethrough and is removably inserted into an inlet end 132 of the hollow tailpiece 112. For example, as illustrated in FIGS. 7 and 7B, an expander ring 134 may be placed over an inlet end 136 of the fluid conduit 128 and the fluid conduit 128 may be threaded through the lumen 133 of the cap 130 outlet end 138 first such that the expander ring 134 frictionally engages with the cap 130 to form a liquid seal therebetween. Other methods of forming a releasable liquid seal between the fluid conduit 128 and the cap 130 may be applied as known in the art. The fluid conduit 128 provides fluid communication between the cap 130 and an interior space 131 of the first fluid impervious container 102.

The lumen 133 disposed through the cap 130 provides the point of entry 126 that includes a horizontal path for entry of human waste into the hollow tailpiece 112, and because the cap 130 is removably connected to the fluid conduit 128, the lumen 133 disposed through the cap 130 also provides a path for entry of human waste into the fluid conduit 128. Because the cap 130 is removably affixed to the inlet end 132 of the hollow tailpiece 112, for example, by a frictional fit or a snap fit, the cap 130 may be disconnected from the inlet end 132 of the hollow tailpiece 112 and pulled away therefrom, as illustrated in FIG. 7B. When the cap is thus removed and pulled away from the inlet end 132 of the hollow tailpiece 112, the fluid conduit 128 connected to the cap 130 slides within the hollow tailpiece 112 and follows the cap 130 to effectively increase the reach of the portable fluid storage device without moving the first fluid impervious container 102.

INDUSTRIAL APPLICABILITY

A portable fluid storage device is presented including a first fluid impervious container and a hollow tailpiece detachably secured to the first fluid impervious container. The hollow tailpiece is angled in such a way to facilitate ease of voiding oneself of waste fluids. A removable second fluid impervious container may be fitted inside an interior space of the first fluid impervious container for collecting fluids. The portable fluid storage device is designed to be taken apart so that the second fluid impervious container may be cleaned or disposed of thereby preventing contamination of the first fluid impervious container or the hollow tailpiece by contact with the fluid.

Numerous modifications to the present disclosure will be apparent to those skilled in the art in view of the foregoing description. Accordingly, this description is to be construed as illustrative only and is presented for the purpose of enabling those skilled in the art to make and use the disclosure and to teach the best mode of carrying out same and is not intended to be exhaustive or to limit the disclosure to the precise form disclosed. It is contemplated that the parts and features of any one of the embodiments described can be interchanged with the parts and features of any other of the embodiments without departing from the scope of the present disclosure. The exclusive rights to all modifications which come within the scope of the appended claims are reserved. All patents, patent publications and applications, and other references cited herein are incorporated by reference herein in their entirety.

I claim:

1. A portable fluid storage device, comprising:
   a fluid impervious container having an interior space for the collection of human waste, the fluid container having an opening at a top end, a broad bottom portion, and a side wall extending there between, the side wall tapering at a constant rate moving from the broad bottom portion to the opening;
   a rigid hollow tailpiece removably extending from the fluid impervious container and providing sealed fluid communication between an inlet end of the hollow tailpiece and the interior space, the hollow tailpiece including a first portion that extends substantially vertically from the fluid impervious container and a second portion that extends at least partially transverse to the first portion;
   a cap removably disposed at the inlet end of the hollow tailpiece and having a lumen disposed therethrough to provide a point of entry for the human waste into the portable fluid storage device such that a horizontal path for entry of the human waste is provided by the lumen disposed through the cap into the hollow tailpiece; and
   a flexible conduit movably disposed within and removable from the hollow tailpiece and having an inlet end removably connected to an outlet end of the cap and an outlet end in fluid communication with the interior space of the fluid impervious container.

2. The portable fluid storage device of claim 1, wherein the rigid hollow tailpiece is removably connected to the fluid impervious container by a threaded compression fitting.

3. The portable fluid storage device of claim 1, wherein the cap and the flexible conduit removably connected thereto may be removed from the inlet end of the hollow tailpiece and pulled away therefrom to extend the reach of the portable fluid storage device.

4. The portable fluid storage device of claim 1 further comprising a handle on the fluid impervious container.

5. A portable fluid storage device, comprising:
   a first fluid impervious container having a first interior space, an opening at a top end, a broad bottom portion and a continuous side wall that tapers at a constant rate moving from the broad bottom portion to the opening;
   a second fluid impervious container removably disposed within the first interior space and having a second interior space for the collection of human waste;
   a rigid hollow tailpiece having a first portion that extends substantially vertically from the first fluid impervious container and a second portion that extends at least partially transverse to the first portion removably extending from the first fluid impervious container and providing sealed fluid communication between an inlet end of the hollow tailpiece and the first interior space; and
   a cap removably disposed at the inlet end of the hollow tailpiece and having a lumen disposed therethrough to provide a point of entry for the human waste into the portable fluid storage device such that a horizontal path for entry of the human waste is provided by the lumen disposed through the cap into the hollow tailpiece.

6. The portable fluid storage device of claim 5, wherein the second fluid impervious container includes a handle.

7. The portable fluid storage device of claim 5 further comprising a deodorizing fluid, gel, or solid applied to the second interior space.

8. The portable fluid storage device of claim 5 further comprising a removable lid disposed over the first interior space, wherein the hollow tailpiece passes through the removable lid from a space exterior to the first fluid impervious container to the first interior space.

9. The portable fluid storage device of claim 8, wherein a gasket forms a seal between the hollow tailpiece and the removable lid.

10. The portable fluid storage device of claim 8, wherein the hollow tailpiece passes through the removable lid from a space exterior to the first fluid impervious container to the second interior space.

11. A portable fluid storage device, comprising:
    a first fluid impervious container having a first interior space, an opening at a top end, a broad bottom portion and a continuous side wall that tapers at a constant rate moving from the broad bottom portion to the opening;
    a second fluid impervious container removably disposed within the first interior space and having a second interior space for the collection of human waste;
    a rigid hollow tailpiece including a first portion that extends substantially vertically from the first fluid impervious container and a second portion that extends at least partially transverse to the first portion removably extending from the first fluid impervious container and providing sealed fluid communication between an inlet end of the hollow tailpiece and the first interior space;
    a cap removably disposed at the inlet end of the hollow tailpiece and having a lumen disposed therethrough to provide a point of entry for the human waste into the portable fluid storage device, such that a horizontal path for entry of the human waste is provided by the lumen disposed through the cap into the hollow tailpiece; and
    a flexible conduit movably disposed within and removable from the hollow tailpiece and having an inlet end removably connected to an outlet end of the cap and an outlet end in fluid communication with the second interior space.

12. The portable fluid storage device of claim 11, wherein the inlet end of the flexible conduit removably connects to the outlet end of the cap by a first sealed connection therebetween and the outlet end of the flexible conduit connects to the second fluid impervious container by a second sealed connection therebetween.

13. The portable fluid storage device of claim 12, wherein the second fluid impervious container is a rigid container sized to fit within the first interior space.

14. The portable fluid storage device of claim 13, wherein the outlet end of the flexible conduit removably connects to the second fluid impervious container.

15. The portable fluid storage device of claim 12, wherein the second fluid impervious container is a flexible bag that is supported by the first interior space.

16. The portable fluid storage device of claim 15, wherein the outlet end of the flexible conduit removably connects to the second fluid impervious container.

* * * * *